(12) United States Patent
Kassab (10) Patent No.: US 9,717,488 B2
(45) Date of Patent: *Aug. 1, 2017

(54) DEVICES AND SYSTEMS FOR INVERTING AND CLOSING THE LEFT ATRIAL APPENDAGE

(71) Applicant: CVDevices, LLC, San Diego, CA (US)

(72) Inventor: Ghassan S. Kassab, San Diego, CA (US)

(73) Assignee: CVDevices, LLC, San Diego ( * ) Notice: Subject to any disclaimer, the term of this patent is extended or adjusted under 35 U.S.C. 154(b) by 188 days.

This patent is subject to a terminal disclaimer.

(21) Appl. No.: 14/338,031

(22) Filed: Jul. 22, 2014

(65) Prior Publication Data

US 2014/0330306 A1 Nov. 6, 2014
US 2017/0065262 A9 Mar. 9, 2017

Related U.S. Application Data

(63) Continuation of application No. 13/537,394, filed on Jun. 29, 2012, now Pat. No. 8,784,469.

(60) Provisional application No. 61/503,428, filed on Jun. 30, 2011.

(51) Int. Cl.
*A61B 17/00* (2006.01)
*A61B 17/12* (2006.01)
*A61B 17/11* (2006.01)
*A61B 17/30* (2006.01)

(52) U.S. Cl.
CPC .... *A61B 17/0057* (2013.01); *A61B 17/12122* (2013.01); *A61B 17/12172* (2013.01); *A61B 2017/00561* (2013.01); *A61B 2017/00575* (2013.01); *A61B 2017/00592* (2013.01); *A61B 2017/00597* (2013.01); *A61B 2017/00623* (2013.01); *A61B 2017/00867* (2013.01); *A61B 2017/1121* (2013.01); *A61B 2017/306* (2013.01)

(58) Field of Classification Search
CPC .......... A61B 17/0057; A61B 17/12122; A61B 17/12172; A61B 2017/00561; A61B 2017/00575; A61B 2017/00592; A61B 2017/00597; A61B 2017/00615; A61B 2017/00623; A61B 2017/00632; A61B 17/12113; A61B 17/12118; A61B 2017/00867; A61B 2017/1121; A61F 2/852

See application file for complete search history.

(56) References Cited

U.S. PATENT DOCUMENTS

6,004,346 A * 12/1999 Wolff ........................ A61F 2/90
623/1.12
7,128,073 B1 10/2006 Van Der Burg et al.
7,727,189 B2 6/2010 VanTassel et al.
2002/0111647 A1 8/2002 Khairkhahan et al.
(Continued)

*Primary Examiner* — Ryan J Severson
*Assistant Examiner* — Christian Knauss
(74) *Attorney, Agent, or Firm* — Reichel Stohry LLP; Mark C. Reichel; Natalie J. Dean (57) ABSTRACT

Devices, systems, and methods for inverting and closing the left atrial appendage. In at least one embodiment of a method for closing a left atrial appendage of the present disclosure, the method comprises the steps of inverting a distal portion of a left atrial appendage, and constraining the inverted distal portion of the left atrial appendage using a device configured to fit within an interior of the left atrial appendage.

20 Claims, 9 Drawing Sheets

(56) References Cited

U.S. PATENT DOCUMENTS

| | | | |
|---|---|---|---|
| 2003/0024527 A1* | 2/2003 | Ginn | A61F 2/00 128/200.24 |
| 2003/0120337 A1 | 6/2003 | Van Tassel et al. | |
| 2003/0181942 A1 | 9/2003 | Sutton et al. | |
| 2003/0191526 A1 | 10/2003 | Van Tassel et al. | |
| 2003/0225443 A1 | 12/2003 | Kiran et al. | |
| 2005/0004652 A1 | 1/2005 | van der Burg et al. | |
| 2005/0038470 A1 | 2/2005 | van der Burg et al. | |
| 2005/0070952 A1 | 3/2005 | Devellian | |
| 2005/0234540 A1 | 10/2005 | Peavey et al. | |
| 2006/0247680 A1 | 11/2006 | Amplatz et al. | |
| 2007/0083230 A1 | 4/2007 | Javois | |
| 2008/0167713 A1 | 7/2008 | Bolling | |
| 2009/0099647 A1 | 4/2009 | Glimsdale et al. | |
| 2010/0160719 A1 | 6/2010 | Kassab et al. | |
| 2010/0204773 A1 | 8/2010 | Elmaleh et al. | |
| 2010/0292776 A1* | 11/2010 | Weber | A61F 2/852 623/1.15 |
| 2011/0022151 A1* | 1/2011 | Shin | A61F 2/04 623/1.11 |
| 2011/0093002 A1* | 4/2011 | Rucker | A61F 2/90 606/198 |
| 2011/0213393 A1* | 9/2011 | Aklog | A61B 17/22 606/159 |
| 2011/0264186 A1* | 10/2011 | Berglung | A61F 2/86 623/1.11 |

* cited by examiner

DEVICES AND SYSTEMS FOR INVERTING AND CLOSING THE LEFT ATRIAL APPENDAGE

PRIORITY

The present application is related to, claims the priority benefit of, and is a U.S. continuation application of, U.S. patent application Ser. No. 13/537,394, filed on Jun. 29, 2012 and issued as U.S. Pat. No. 8,784,469 on Jul. 22, 2014, which is related to, and claims the priority benefit of, U.S. Provisional Patent Application Ser. No. 61/503,428, filed Jun. 30, 2011, the contents of which are incorporated by reference in their entirety into this disclosure.

BACKGROUND

The present disclosure relates generally to medical devices and methods, such as those useful for inverting and closing a left atrial appendage.

Atrial fibrillation (AF) is the most common cardiac arrhythmia and affects millions of people worldwide, with the incidence expected to increase significantly in coming years. While AF is not a serious cardiac risk factor, it is very significant risk factor for stroke. AF produces a large number of arterial emboli that can enter cerebral circulation and cause stroke. AF is estimated to cause about 25% of all strokes and increases the risk of stroke in an individual by 500% when compared to people with normal sinus rhythm. Over 90% of such embolic strokes originate with clots released from the left atrial appendage (LAA), and a number of procedures and tools have been developed in an attempt to isolate the left atrial appendage and reduce the incidence of stroke, particularly in people suffering from AF.

The left atrial appendage is a windsock-like structure which extends from the left atrium and creates a side chamber which can be a site of increased clot formation and accumulation. There is some evidence that AF can further increase the tendency for clot to accumulate in the LAA, and the rapid contraction of the heart which accompanies AF can initiate the release of emboli and the consequent risk of stroke.

Both percutaneous and intravascular approaches have been proposed for LAA closure. Although some of these devices have now received regulatory approval, such systems are subject to a number of potential drawbacks. In particular, the present systems may be subject to incomplete LAA closure, dislodgement of the device, blood clot formation on the device, and the like. For these reasons, it would be desirable to provide improved LAA closure devices and protocols which produce at least some of these risks.

BRIEF SUMMARY

In at least one embodiment of a system for occluding a left atrial appendage of the present disclosure, the system comprises a vacuum tube defining a vacuum tube lumen therethrough, the vacuum tube having a suction flange at its distal end, a catheter configured for introduction into a mammalian blood vessel and advancement to a left atrium, the catheter comprising an elongated tubular body defining a central lumen therethrough and further comprising a balloon configured for inflation and deflation, the central lumen configured to slidably receive the vacuum tube therein, and a double stent assembly configured for placement upon the balloon, the double stent assembly comprising an outer scaffold configured for expansion and to be anchored within an interior of a left atrial appendage, and an inner scaffold positioned within the outer scaffold and configured for expansion within the outer scaffold and further configured to receive and engage a distal portion of the left atrial appendage after inversion of the distal portion of the left atrial appendage. In another embodiment, the double stent assembly further comprises an occluder membrane coupled to the outer scaffold, the occluder membrane configured to occlude an orifice of the left atrial appendage upon expansion of the occluder membrane. In yet another embodiment, wherein the occluder membrane comprises a valve configured to receive the catheter and further configured to be sealed upon removal of the catheter. In an additional embodiment, when a vacuum is applied through the vacuum tube and the suction flange is attached to the distal portion of the left atrial appendage, the vacuum tube can be withdrawn in a direction away from the distal portion to invert the distal portion.

In at least one embodiment of a system for occluding a left atrial appendage of the present disclosure, the system further comprises a guidewire configured for positioning within one or both of the vacuum tube lumen and/or the central lumen of the catheter. In an additional embodiment, the outer scaffold is configured for self-expansion within the interior of the left atrial appendage and further configured to conform to dimensions of the interior of the left atrial appendage. In yet an additional embodiment, the system further comprises a sheath configured for placement around at least part of the catheter and further configured to receive the double stent assembly in a compressed configuration therein. In another embodiment, the system further comprises one or more tethers coupled to the outer scaffold and the inner scaffold, the one or more tethers configured to retain the inner scaffold within the outer scaffold.

In at least one embodiment of a system for occluding a left atrial appendage of the present disclosure, the system further comprises one or more memory arms coupled to the outer scaffold or the occluder membrane, the one or more memory arms configured to receive and retain at least a portion of the left atrial appendage. In another embodiment, the system further comprises a flap membrane coupled to the outer scaffold or the occluder membrane, the flap membrane configured to cover the one or more memory arms. In yet another embodiment, the system further comprises a vacuum source coupled to the vacuum tube, the vacuum source operable to generate a vacuum within the vacuum tube lumen to facilitate engagement of the distal portion of the left atrial appendage using the suction flange of the vacuum tube, and an inflation source coupled to the catheter, the vacuum source operable to inflate and/or deflate the balloon.

In at least one embodiment of a system for occluding a left atrial appendage of the present disclosure, the system comprises a vacuum tube defining a vacuum tube lumen therethrough, the vacuum tube having a suction flange at its distal end, a catheter configured for introduction into a mammalian blood vessel and advancement to a left atrium, the catheter comprising an elongated tubular body defining a central lumen therethrough and further comprising a balloon configured for inflation and deflation, the central lumen configured to slidably receive the vacuum tube therein, a double stent assembly configured for placement upon the balloon, the double stent assembly comprising an outer scaffold configured for expansion and to be anchored within an interior of a left atrial appendage, an inner scaffold positioned within the outer scaffold and configured for expansion within the outer scaffold and further configured to receive and engage a distal portion of the left atrial appendage after inversion of the distal portion of the left atrial appendage, and an occluder membrane coupled to the outer scaffold, the occluder membrane configured to occlude an orifice of the left atrial appendage upon expansion of the occluder membrane, and one or more memory arms coupled to the outer scaffold or the occluder membrane, the one or more memory arms configured to receive and retain at least a portion of the left atrial appendage.

In at least one embodiment of a method for closing a left atrial appendage of the present disclosure, the method comprises the steps of inverting a distal portion of a left atrial appendage, and constraining the inverted distal portion of the left atrial appendage using a device configured to fit within an interior of the left atrial appendage. In another embodiment, the step of constraining is performed to facilitate closure of an orifice defined by the left atrial appendage and to prevent emboli present within the interior of the left atrial appendage from release therefrom into a left atrium. In yet another embodiment, the step of constraining is performed to promote closure of an orifice defined by the left atrial appendage and to promote fibrosis. In an additional embodiment, the step of inverting comprises introducing a vacuum tube having a suction flange at its distal end into the interior of the left atrial appendage, applying suction through the vacuum tube so that the suction flange engages the distal portion of the left atrial appendage, and withdrawing the vacuum tube in a direction away from the distal portion of the left atrial appendage to invert the distal portion of the left atrial appendage.

In at least one embodiment of a method for closing a left atrial appendage of the present disclosure, the step of constraining comprises introducing the device into the interior of the left atrial appendage, the device comprising a double stent assembly having an outer scaffold and an inner scaffold positioned within the outer scaffold, expanding the outer scaffold within the interior of the left atrial appendage to anchor the outer scaffold, expanding the inner scaffold to form a central opening therein, positioning the inverted distal portion of the left atrial appendage within the central opening of the inner scaffold, and closing the inner scaffold to engage the inverted distal portion of the left atrial appendage. In an additional embodiment, the step of expanding the outer scaffold further comprises expansion of an occluder membrane coupled to the outer scaffold, whereby the expanded outer scaffold is configured to occlude an orifice of the left atrial appendage. In yet an additional embodiment, the step of introducing the device into the left atrial appendage is performed by introducing the double stent assembly into the left atrial appendage using a balloon catheter, wherein the step of expanding the outer scaffold is performed by inflating the balloon, wherein at least a portion of the balloon catheter is positioned within the left atrial appendage and through a valve defined within the occluder membrane upon expansion of the outer scaffold, and wherein the method further comprises the step of withdrawing the at least a portion of the balloon catheter from the valve, wherein the valve self-closes upon withdrawal of the at least a portion of the balloon catheter. In another embodiment, the method further comprises the step of receiving and retaining at least a portion of the left atrial appendage using one or more memory arms coupled to the device.

In at least one embodiment of a method for closing a left atrial appendage of the present disclosure, the method comprises inverting at least a portion of the LAA while an orifice opening to the LAA is occluded to prevent emboli release.

The inverted LAA is then closed by circumferentially constraining an inverted surface thereof to promote full closure and fibrosis.

In various aspects of the method, inverting comprises positioning an emboli barrier over the orifice leading to the interior of the LAA, capturing an apical region of the LAA with a tool positioned through the emboli barrier, and drawing the tool proximate to pull the apical region in order to at least partially invert the LAA. By "inverting" the LAA, it is meant that apex or other portion of the apical region is drawn proximally inwardly (toward the left atrium) into the interior volume of the LAA. In at least one embodiment, the apex of the LAA will not be drawn completely into the interior of the left atrium, and in particular the inwardly disposed, inverted portion of the LAA will not be brought past the emboli barrier which lies across the LAA orifice.

In other aspects/embodiments of the present disclosure, the emboli barrier will be positioned by releasing a self-expanding scaffold to deploy the barrier over the LAA orifice. The scaffold may be constructed in a manner similar to a self-expanding stent and may be shaped to conform to the expected geometry of the LAA orifice, e.g. being oval shaped with a mean diameter in the range from 10 mm to 24 mm. The scaffold may be fabricated from a wide variety of elastic materials, usually being elastic metals, such as stainless steel, nickel-titanium alloy, cobalt-chromium-alloys, nickel-molybdemun-iron-alloys, tantalum, and the like. While metals are generally preferred, the scaffold can also be formed from shape-memory polymers, such as polyurethanes, PTFEs, and the like.

In various aspects of the method, capturing the apical region of the LAA comprises advancing a capture catheter through the deployed barrier to engage the LAA apex or other epical region, allowing the catheter to be pulled back to effect the desired inversion. The capture catheter will typically apply a vacuum to adhere to the LAA apex, but other capture implements, such as barbs, jaw-like devices, and the like, can also be used.

Circumferential containment of the inverted LAA may be effected by a variety of techniques. Typically, the LAA will be constrained using a self-closing scaffold which is placed to collapse over the inverted portion of the LAA lying within the interior of the LAA. Other cages, frames, suture devices, or the like, could also be used to constrain the inverted segment of the LAA.

In at least one embodiment of a system for closing a left atrial appendage of the present disclosure, the system comprises a catheter adapted to be advanced into a left atrium, a barrier deployable from the catheter and adapted to be deployed across an orifice of the left atrium, an apical capture device on the catheter adapted to engage an apical region of the LAA and draw the engaged apical region proximally toward the orifice to invert the LAA, and a circumferential constraint deployable from the catheter adapted to be deployed over the inverted LAA to promote closure and fibrosis.

In particular aspects of the system, the catheter may be adapted to be introduced over a guide wire which may be placed intravascularly through the right atrium, the atrial septum, and into the left atrium. Alternatively, the catheter could be adapted for transparent introduction. The catheter will typically comprise a tubular body having a central lumen, and the apical capture device usually comprises a vacuum tube slidably disposed in the central lumen of the tubular body. The barrier usually comprises a self-expending scaffold, generally as described above in connection with the methods of the present disclosure, which carries a membrane thereon. The scaffold is adapted to expand and conform to the LAA orifice in order to deploy the membrane across the LAA orifice opening. The membrane, in various embodiments, will have a self-closing valve which receives the catheter and allows the catheter to be positioned through the membrane and ultimately removed from the membrane. The valve will be self-closing so that, when the catheter is withdrawn, the membrane will form a complete barrier to prevent emboli release. In further aspects, the circumferential constraint comprises a self-closing scaffold, where the scaffold will typically be placed over an inflatable balloon which allows the scaffold to be temporarily opened in order to allow the inverted portion of the LAA to be pulled into the scaffold by the apical capture device. The balloon then may be deflated to allow the self-closing scaffold to close over and constrain the inverted portion of the LAA.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

Figure 1A:
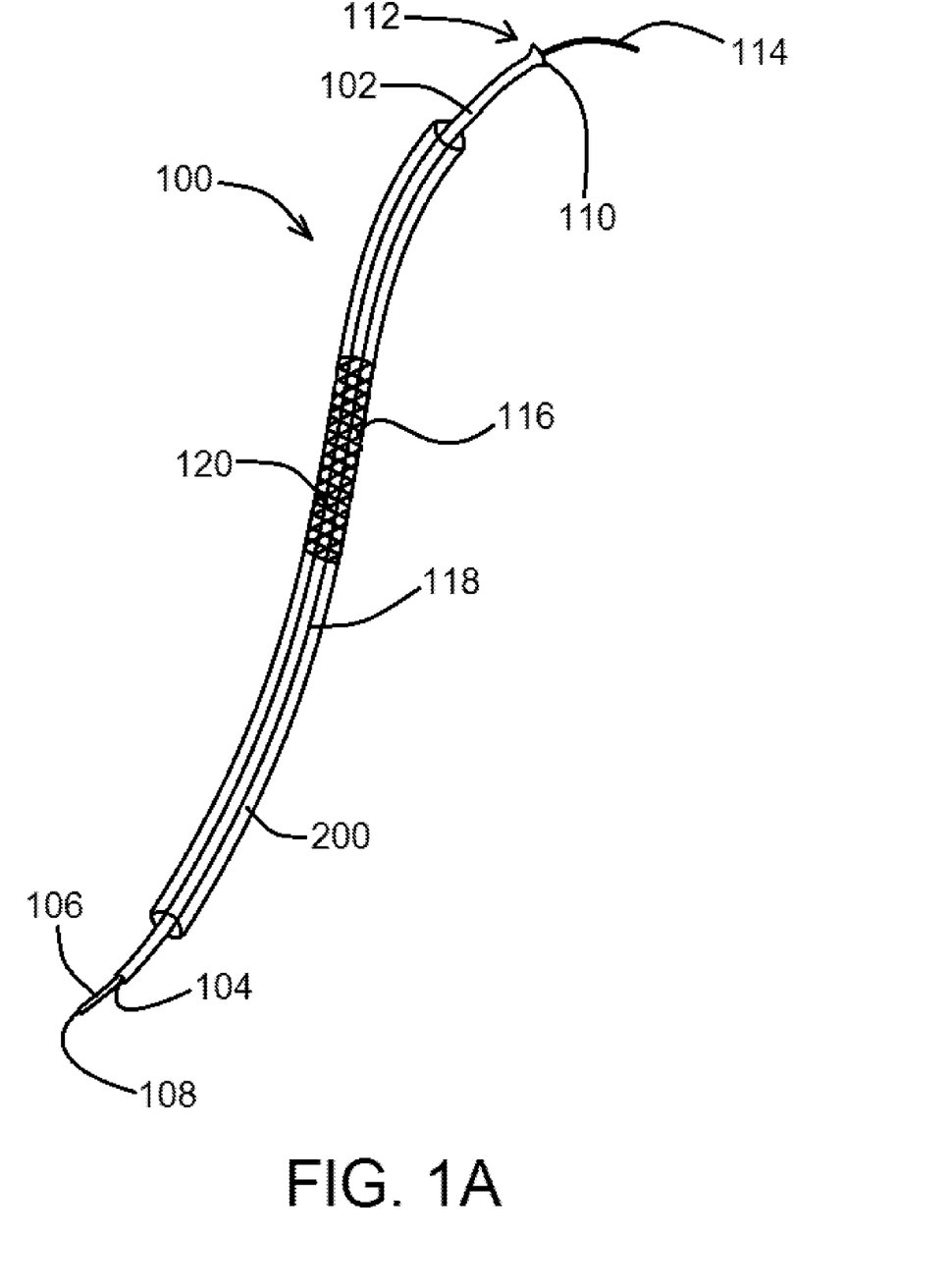
FIG. 1A shows portions of a catheter system useful to invert a left atrial appendage, according to an exemplary embodiment of the present disclosure.

An exemplary catheter system for inverting closure of the left atrial appendage (LAA) of a heart of the present disclosure is shown in FIG. 1. As shown in FIG. 1A, an exemplary catheter system 100 constructed in accordance with the principles of the present disclosure comprises an elongated tubular body 102 defining a central passage or lumen 104 therethrough. A vacuum tube 106, in at least one embodiment, may be slidably disposed within the central lumen 104 of the tubular body 102, with vacuum tube 106 defining its own lumen 108 therethrough and having a suction flange 110 at the distal end 112 of vacuum tube 106. The vacuum tube 106 is connectible to a vacuum source 1100 (not shown in FIG. 1A but shown in the general system figure in FIG. 11) so that vacuum (or negative pressure) can be applied through the lumen 108 of the vacuum tube 106 in order to allow the suction flange 110 to engage and adhere to the target site on the interior wall of the LAA, which may be at or near the apex of LAA. Vacuum tube 106, in at least one embodiment, may include a lumen for receiving a guidewire 114. A double stent assembly 116, as shown in FIG. 1A and referenced in further detail herein, can be carried on the exterior surface 118 of the tubular body 102 and delivered into the patient as described further herein.

Figure 1B:
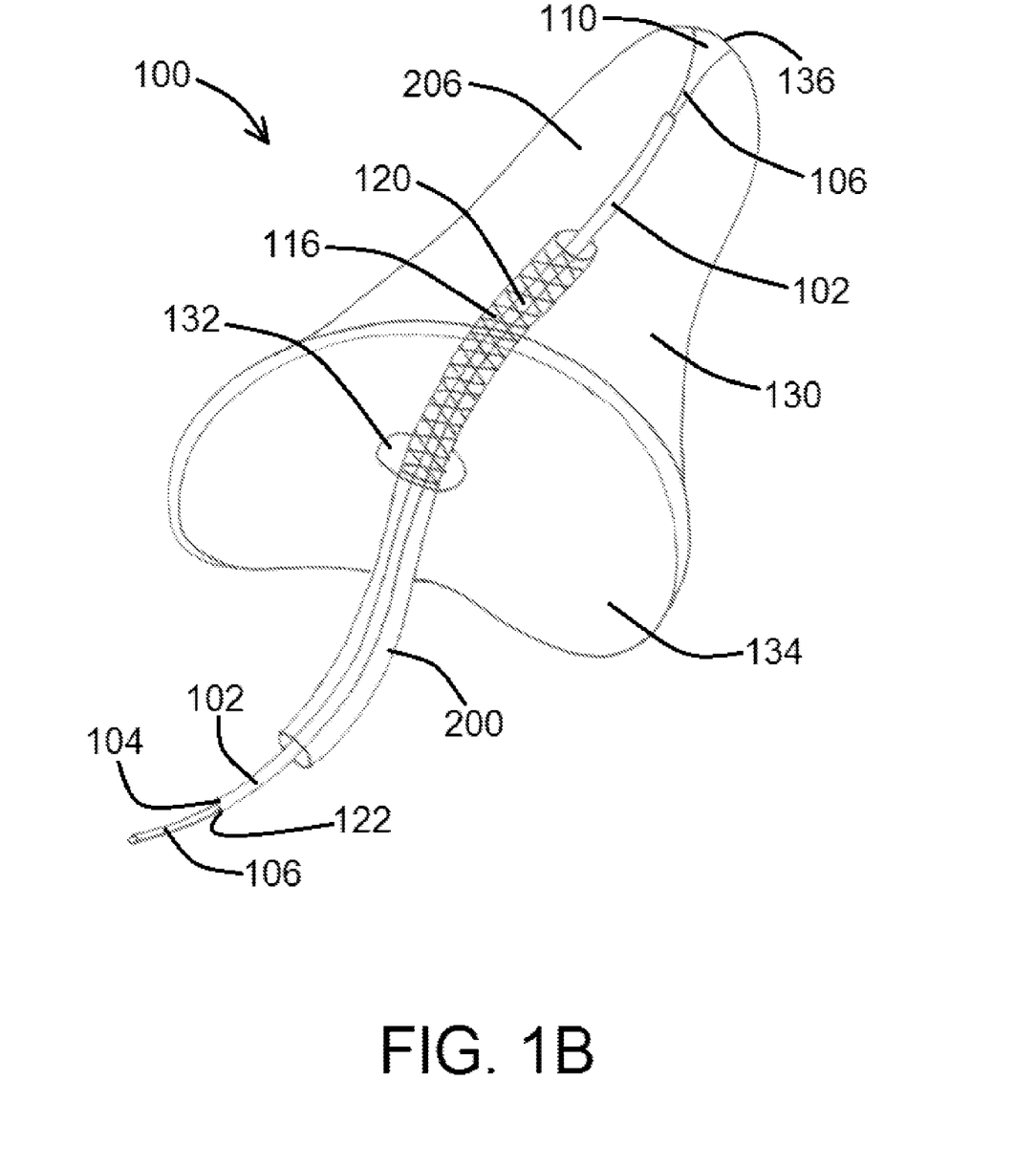
FIG. 1B shows portions of a catheter system positioned within a left atrial appendage, according to an exemplary embodiment of the present disclosure.

As described in additional detail below, an exemplary double stent assembly 116 of the present disclosure includes an outer, self-expanding scaffold (stent) 202 which is maintained in a constrained or radially collapsed configuration by an outer sheath 200 configured to slidably engage tubular body 102 as shown in FIG. 1A. A balloon 120, coupled to tubular body 102, is configured to expand at least one of the stents of the double stent assembly 116, by way of inflation of balloon 120 using an inflation source 1102 (not shown in FIG. 1A but shown in the general system figure in FIG. 11). Balloon 120 inflation, in at least one embodiment, may occur by way of inflation either through an inflation lumen 122 of tubular body 102 separate from central lumen 104, as shown in FIG. 1B for example, through central lumen 104, or through a separate inflation tube 124 (shown in FIG. 2A), so that a gas, a liquid, and/or another substance 126 can be delivered through one or more of inflation lumen 122, central lumen 104, and/or inflation tube 124, through an optional aperture 128 defined within tubular body 102 or balloon 120 itself, and into balloon 120. Deflation would be the opposite of inflation, whereby the gas, liquid, and/or substance 126 would exit balloon 120 through optional aperture 128.

Referring now to FIG. 1B, an exemplary catheter system 100 of the present disclosure may be deployed into the interior of the LAA 130 through the LAA orifice 132 within the left atrium wall 134. The suction flange 110 of the vacuum tube 106 may then engage the inner wall of the LAA 130, optionally within an apical region at or near the LAA apex 136, by way of suction from a vacuum source operably coupled to the vacuum tube.

Figure 2A:
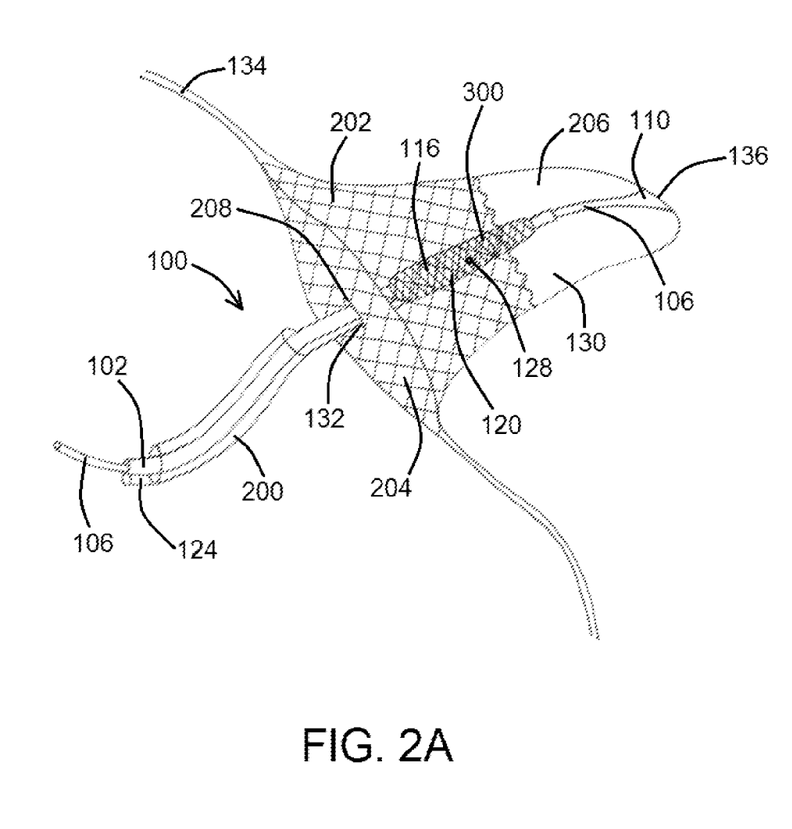
FIG. 2A shows portions of a catheter system positioned within a left atrial appendage with a deployed/expanded outer scaffold, according to an exemplary embodiment of the present disclosure.
Figure 2B:
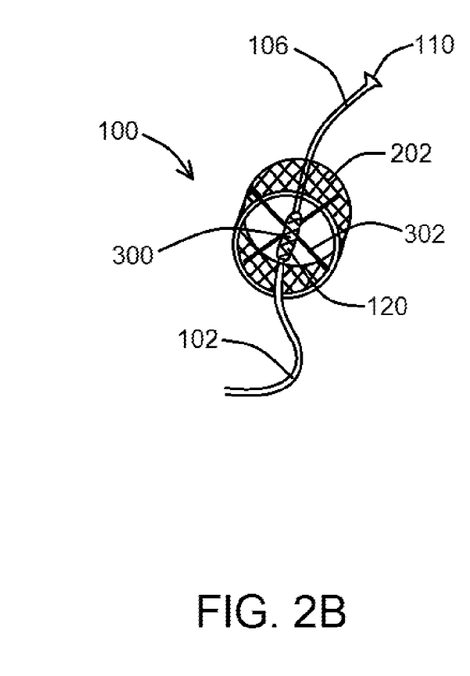
FIG. 2B shows portions of a catheter system with a deployed/expanded outer scaffold, according to an exemplary embodiment of the present disclosure.

Referring now to FIGS. 2A and 2B, after the tubular body 102 of the catheter system 100 has been properly positioned within the LAA 130, a sheath 200 surrounding at least part of tubular body 102 may be retracted away from the relative distal end of tubular body 102, allowing an outer scaffold 202 (which may be referred to herein as an "outer stent") of the double stent assembly 116 to expand and anchor within a region of the LAA 130 adjacent to the LAA orifice 132. The outer scaffold 202 carries and deploys an occluder membrane 204 across the LAA orifice 132 in order to inhibit or prevent emboli release during the closure process (such as during subsequent steps of exemplary methods/protocols as referenced herein) as well as permanently isolating the interior 206 of the LAA 130 after the methods/protocols has/have been completed. Occluder membrane 204, in various embodiments, may be composed of a variety of conventional and biocompatible materials capable of blocking the passage of emboli, including, but not limited to, various polytetrafluoroethylenes (PTFEs), polyurethanes, silicone rubbers, Dacron, and/or various biologic materials such as bovine pericardium, and the like.

Occluder membrane 204, in at least one embodiment, has a valve 208, which may be at or near the relative center of occluder membrane 204, which is configured to receive tubular body 102 and, as described in further detail below, allows the tubular body 102 to be removed at the end of the method/protocol. In at least one embodiment, valve 208 is self-closing so that after tubular body 102 has been removed, passage through valve 208 is fully closed and occluder membrane 204 is fully occlusive to the passage of emboli from the interior 206 of LAA 130. Suitable self-closing valves 208, by way of example, include but are not limited to flap valves, duck-billed valves, slit valves, and the like.

Figure 3A:
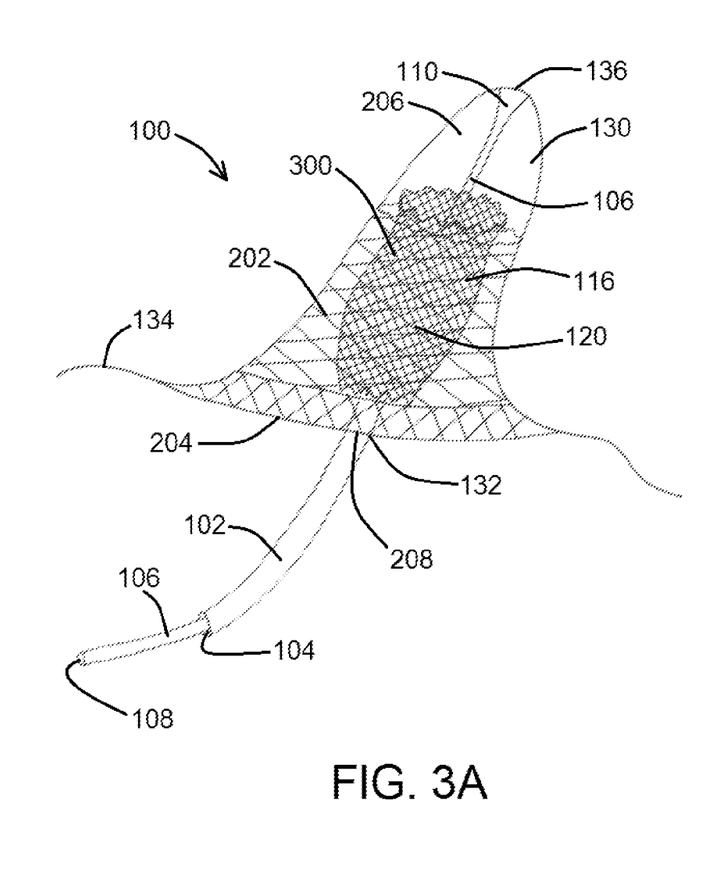
FIG. 3A shows portions of a catheter system positioned within a left atrial appendage with deployed/expanded outer and inner scaffolds, according to an exemplary embodiment of the present disclosure.
Figure 3B:
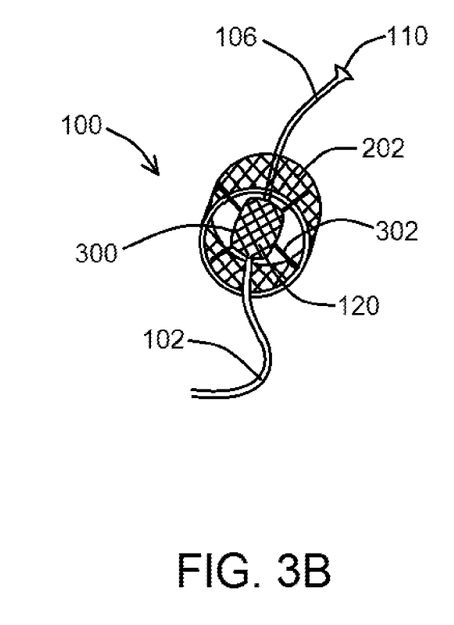
FIG. 3B shows portions of a catheter system with deployed/expanded outer and inner scaffolds, according to an exemplary embodiment of the present disclosure.

Referring now to FIGS. 3A and 3B, and either before or after occluder membrane 204 has been deployed, an inner scaffold 300 (which may be referred to herein as an "inner stent") is deployed, which may be by inflating balloon 120 on tubular body 102 which carries inner scaffold 300. A plurality of cables or tethers 302, in at least one embodiment, are provided between outer scaffold 202 and inner scaffold 300, as shown in FIG. 3A. Cables or tethers 302, in at least one embodiment, are configured to hold inner scaffold 300 in place after the tubular body 102 is removed.

Figure 4A:
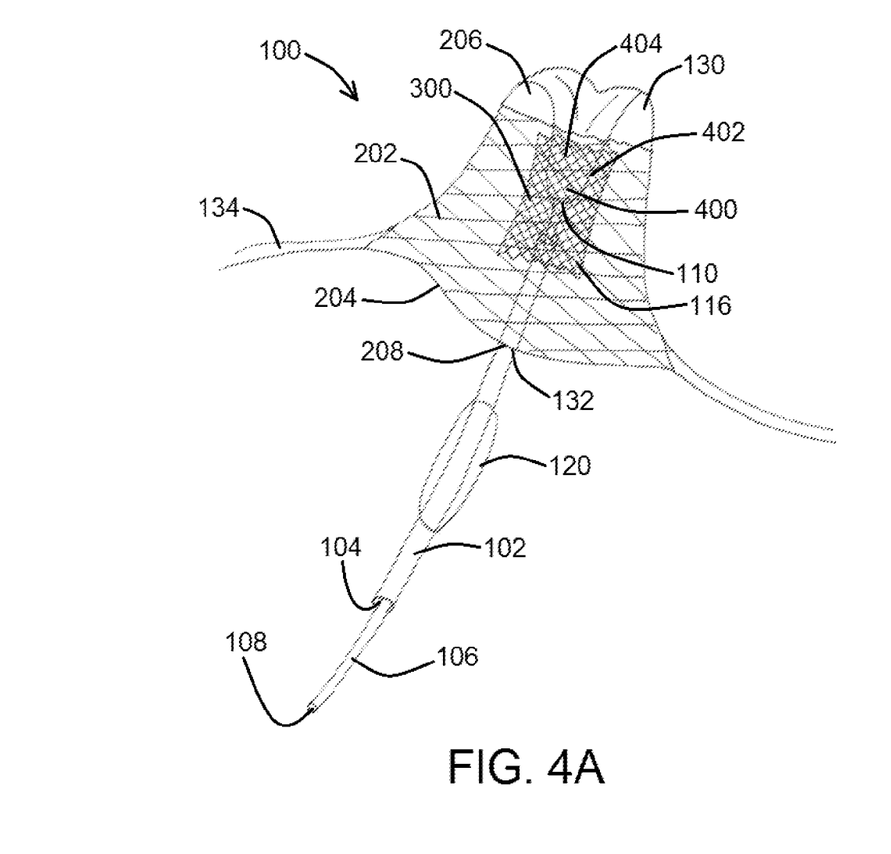
FIG. 4A shows portions of a catheter system positioned within a left atrial appendage with deployed/expanded outer and inner scaffolds and a portion of the left atrial appendage positioned within the inner scaffold, according to an exemplary embodiment of the present disclosure.
Figure 4B:
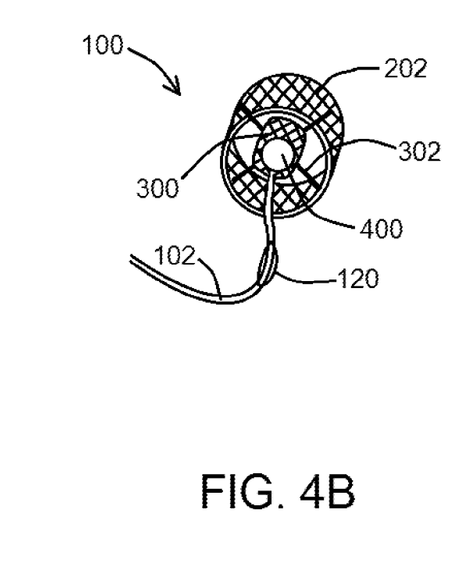
FIG. 4B shows portions of a catheter system with deployed/expanded outer and inner scaffolds and a portion of the left atrial appendage positioned within the inner scaffold, according to an exemplary embodiment of the present disclosure.

As shown in FIGS. 4A and 4B, after inner scaffold 300 has been expanded by balloon 120, balloon 120 may be deflated and tubular body 102 may be withdrawn from the patient. During or after withdrawal, vacuum or suction from vacuum source 1100 may be applied through vacuum tube 106 while suction flange 110 is reversibly affixed to LAA 130 in order to invaginate or invert a distal portion 400 of a wall 402 of the LAA 130. The inverted portion of wall 402, in at least one embodiment, may then be drawn into a central opening 404 defined within the expanded inner scaffold 300 while outer scaffold 202 maintains the position of the inner scaffold 300, using, for example, cables or tethers 302.

Figures 5, 6A, 6B, 7:
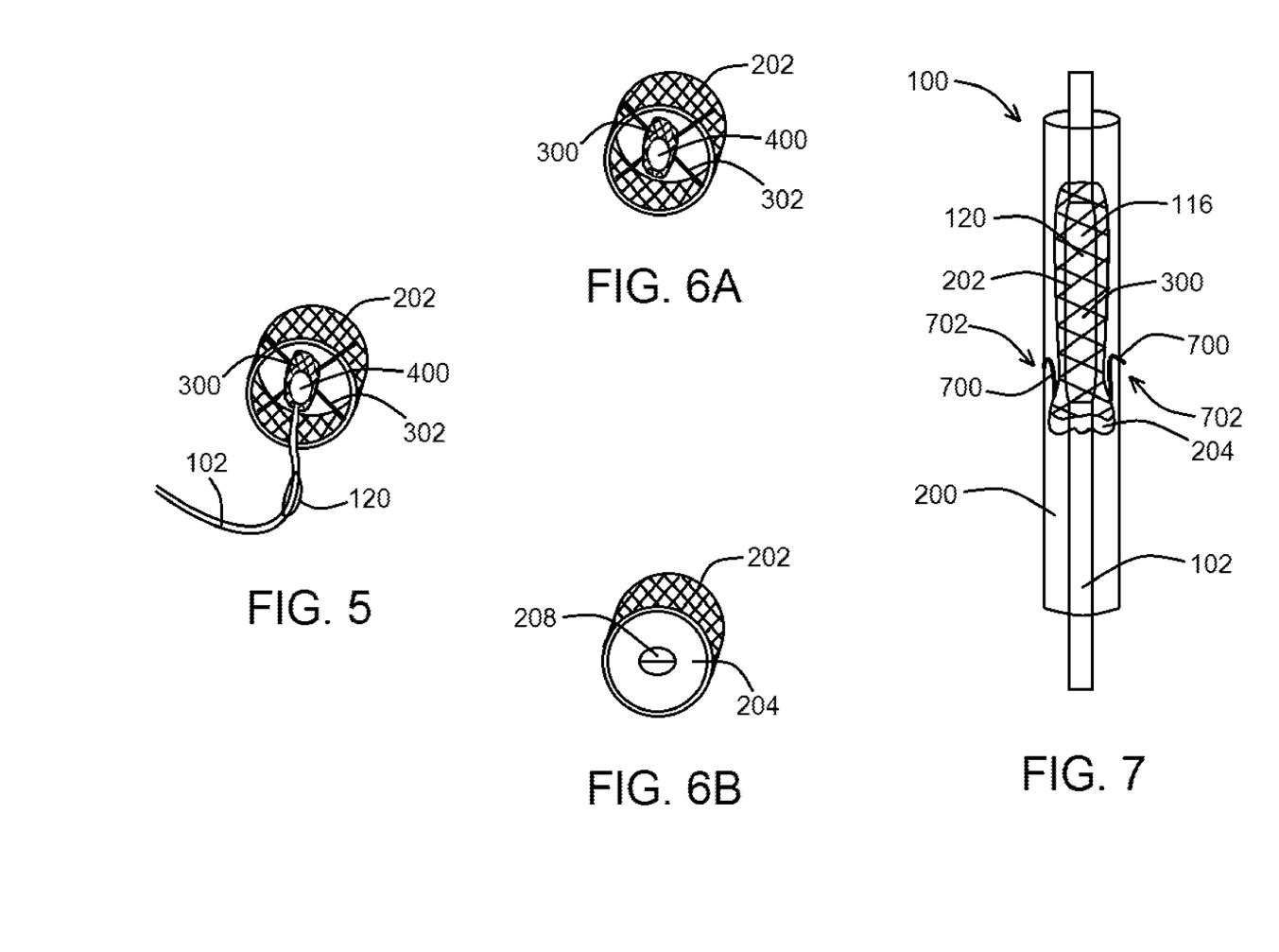
FIG. 5 shows an inner scaffold closed over the invagination or inverted portion of the left atrial appendage wall after the balloon has been deflated and withdrawn, according to an exemplary embodiment of the present disclosure.
FIG. 6A shows an inner scaffold closed over the invagination or inverted portion of the left atrial appendage wall after the balloon catheter has been withdrawn, according to an exemplary embodiment of the present disclosure.
FIG. 6B shows an expanded outer scaffold with an occluder membrane covering one end and a valve positioned within the occluder membrane, according to an exemplary embodiment of the present disclosure.
FIG. 7 shows portions of a catheter system useful to invert a left atrial appendage, according to an exemplary embodiment of the present disclosure.

Referring now to FIG. 5, after the distal portion 400 of LAA 130 has been drawn into the central opening 404 of inner scaffold 300, inner scaffold 300 will be allowed to close in over the distal portion 400 of LAA 130 in order to fully circumscribe and close that portion 400. Such inversion and circumferential closure will cause the tissue to fibrose over time, thus further reducing the risk of emboli formation and release from the occluded LAA 130. In at least one embodiment, inner scaffold 300 is self-closing. In at least another embodiment, A circumferentially constraining the inverted LAA comprises allowing a self-closing scaffold (such as inner scaffold 300) to collapse over the inverted LAA.

In at least one embodiment, and before or while the vacuum tube 106 is drawing the LAA 130 inwardly to invert LAA 130, the applied vacuum will also be drawing blood and other fluids from the interior 206 of LAA 130 to further encourage closure and allow for the volume reduction of the interior 206 of LAA 130 as it is being inverted.

After LAA 130 has been fully inverted, portions of catheter assembly 100 (such as tubular body 102 and vacuum tube 106) will be withdrawn through valve 208, leaving valve 208 closed and the occluder membrane 204 completely sealed off, as shown in FIGS. 6A and 6B. In a number of the previous figures, membrane 204 is not shown in order to provide an improved view of the interior of the double stent assembly 116. After membrane 204 has been deployed as referenced above, it remains in place (unless intentionally removed) in order to prevent emboli release during and after the implantation process. However, once tubular body 102 is withdrawn, valve 208 will close and the interior 206 of LAA 130 will be fully isolated from the left atrium.

In various embodiments of the present disclosure, it would be desirable to provide an exemplary catheter system 100 with an improved sealing mechanism about the periphery of the membrane to promote complete sealing of the interior of the LAA, particularly during the initial stages of the device deployment. As referenced herein, a "device" may comprise a double stent assembly of the present disclosure, and potentially additional components of an exemplary catheter system 100. For example, as shown on FIG. 7, portions of an exemplary catheter system 100 of the present disclosure comprise an occluder membrane 204 carried by a double stent assembly 116, disposed over a balloon 120, as generally described above/herein in connection with various other embodiments, and may include a sealing mechanism about its periphery in order to provide enhanced performance and sealing about the orifice 132 of the LAA 130. As shown in FIG. 7, the enhanced seal may comprise one or more memory arms 700 (which may be an exemplary component of a memory flap 702, described in further detail herein) which are configured to capture and evert tissue about the LAA 130. Memory flap(s) 700 and occluder membrane 204 are initially constrained around the catheter (tubular body 102), typically by an external sheath 200 as shown in the figure. When sheath 200 is retracted to deploy the outer stent/scaffold 300 (as described in connection the previous embodiments), occluder membrane 204 and memory flap(s) 700 will deploy, as shown in FIG. 8.

Figure 8:
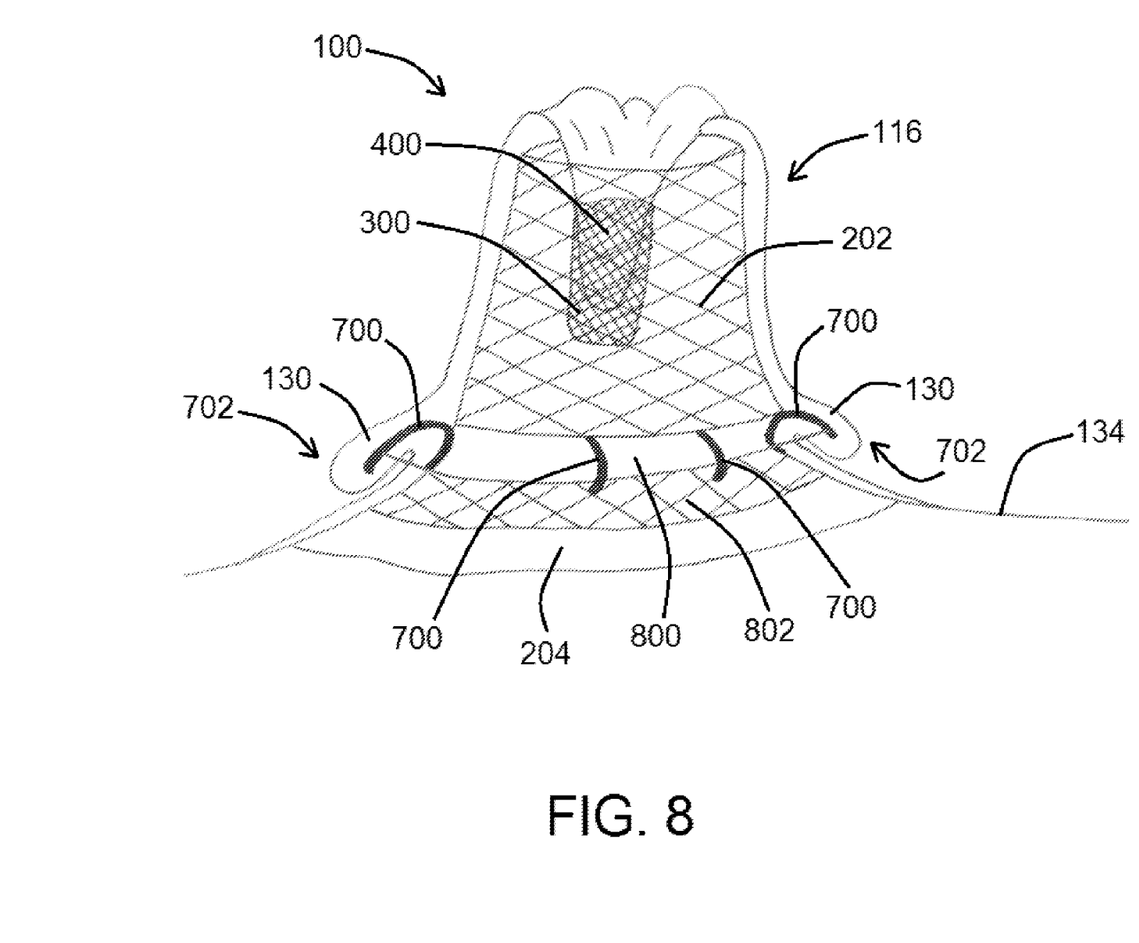
FIG. 8 shows a double stent assembly having memory arms and a flap membrane to seal against atrial wall or left atrial appendage tissue, according to an exemplary embodiment of the present disclosure.
Figure 9:
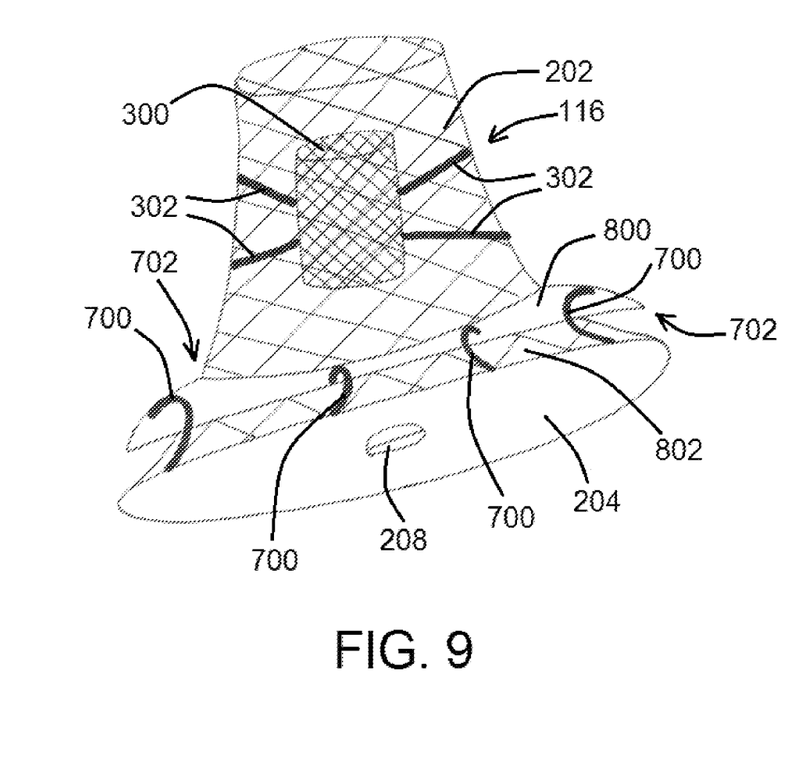
FIG. 9 shows a double stent assembly having memory arms and a flap, according to an exemplary embodiment of the present disclosure.

In at least one embodiment, and as shown in FIGS. 8 and 9, an exemplary memory flap 702 comprises a plurality of memory arms 700 and a flap membrane 800 mounted over memory arm(s) 700, wherein memory arms 700 can deploy outwardly to entrap LAA tissue 130 surrounding LAA orifice 132. In at least one embodiment, a flange portion of memory flap 702 extends from a lower portion of flap membrane 800 upwards and helps to position flap membrane 800 across LAA orifice 132 to provide the primary occlusion.

Figure 10:
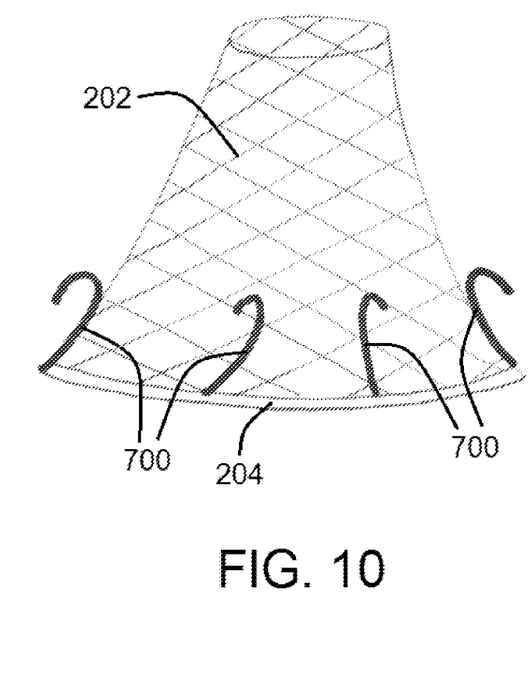
FIG. 10 shows an outer scaffold and an occluder membrane with memory arms extending therefrom, according to an exemplary embodiment of the present disclosure.

With reference the embodiments of portions of catheter systems 100 of the present disclosure shown in FIGS. 9 and 10, it can be seen that the memory arms 700 can be deployed downwardly in order to oppose the LAA 130 tissue and would typically form a part of a cylindrical external metallic self-expanding stent. Simple memory arm 700 material may include, but is not limited to, stainless steel, cobalt-chromium-nickel-molybdenum-iron alloys, tantalum, nitinol, nickel-titanium, polymer materials, and shape-memory polymers, such as polyurethanes, polytetrafluroethylenes, or other materials as described above.

Deployment of the double stent assemblies 116 as shown in FIGS. 7-9 (and the outer scaffold 202 shown in FIG. 10) may occur as referenced above in connection with other embodiments. However, in at least one embodiment, when flap membrane 800 is retracted, memory arm(s) 700 will deploy to place the flap membrane 800 downwardly to entrap the LAA 130 tissue in order to deploy the enhanced seal about occluder membrane 204. Such an embodiment has several advantages including the enhanced sealing as discussed above, an enhanced reinforcement or support of the occluder membrane 204, and for overall support for the deployed mechanism. Exemplary flap membrane 800 embodiments can also act as extension of the primary occluder membrane 204 to increase the LAA orifice 132 coverage.

Figure 11:
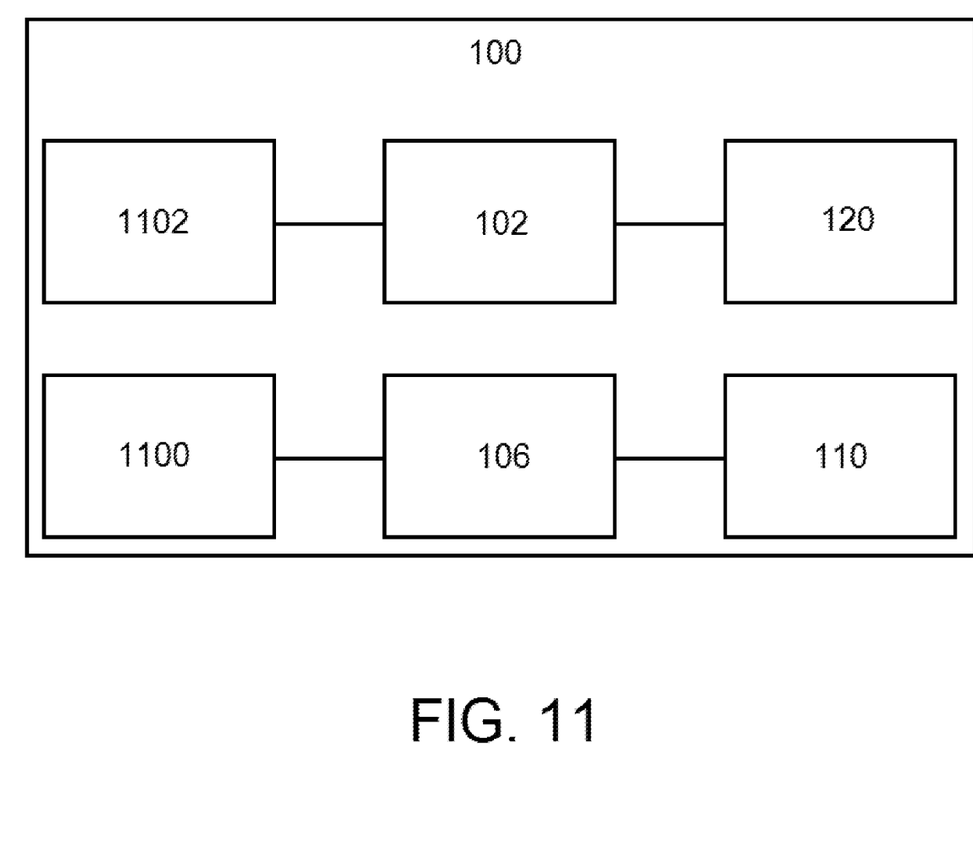
FIG. 11 shows a block diagram of components of a catheter system, according to an exemplary embodiment of the present disclosure.

FIG. 11 shows a block diagram of certain components of an exemplary catheter system 100 of the present disclosure. As shown therein, an exemplary catheter system 100 comprises an elongated tubular body 102 coupled to an inflation source 1102, with a balloon 120 coupled to the tubular body 102, so that inflation and deflation can occur using inflation source 1102. Further, an exemplary vacuum tube 106 is shown coupled to an exemplary vacuum source 1100, so that operation of vacuum source 1100 causes a vacuum within vacuum tube to facilitate engagement of a portion of a left atrial appendage 130 using suction flange 110. Additional components, as referenced herein, may comprise various embodiments of catheter systems 100.

While various embodiments of systems and devices for inverting and closing a left atrial appendage and methods of using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A double stent assembly for occluding a left atrial appendage, the double stent assembly comprising:
   an outer scaffold configured for expansion and to be anchored within an interior of a left atrial appendage;
   an inner scaffold coupled to the outer scaffold via one or more tethers, comprising a body extending between a proximal end and a distal end, and defining a central opening therethrough, the inner scaffold positioned within the outer scaffold and the body configured for expansion within the outer scaffold and further configured to receive and engage a distal portion of the left atrial appendage within the central opening after inversion of the distal portion of the left atrial appendage; and
   an occluder membrane coupled to the outer scaffold, the occluder membrane configured to occlude an orifice of the left atrial appendage upon expansion of the occluder membrane and inhibit bidirectional flow therethrough;
   wherein the body of the inner scaffold does not apply direct radial pressure to the outer scaffold when both the outer scaffold and the inner scaffold are expanded.

2. The double stent assembly of claim 1, wherein the double stent assembly is configured for placement upon a balloon coupled to a catheter such that inflation of the balloon expands the body of the inner scaffold.

3. The double stent assembly of claim 1, wherein the outer scaffold is configured for self-expansion within the interior of the left atrial appendage and further configured to conform to the interior of the left atrial appendage.

4. The double stent assembly of claim 1, wherein the occluder membrane is configured to prevent emboli from within the interior of the left atrial appendage from being released from the interior of the left atrial appendage.

5. The double stent assembly of claim 1, wherein the occluder membrane comprises a valve configured to receive a catheter therethrough.

6. The double stent assembly of claim 5, wherein the valve is a self-closing valve.

7. The double stent assembly of claim 1, wherein the one or more tethers are configured to retain the inner scaffold within the outer scaffold.

8. The double stent assembly of claim 1, wherein the inner scaffold is configured for expansion due to inflation of a balloon of a balloon catheter.

9. The double stent assembly of claim 1, wherein the inner scaffold is configured to retain a distal portion of a wall of the left atrial appendage when the distal portion is present within the central opening of the inner scaffold.

10. The double stent assembly of claim 1, further comprising:
    one or more memory arms coupled to the outer scaffold or the occluder membrane, the one or more memory arms configured to receive and retain at least a portion of the left atrial appendage.

11. A system for occluding a left atrial appendage, the system comprising:
- a catheter having a balloon positioned thereon, the catheter configured for introduction into a mammalian blood vessel and advancement to a left atrium; and
- a double stent assembly configured for placement upon the balloon, the double stent assembly comprising an outer scaffold configured for expansion and to be anchored within an interior of a left atrial appendage, and an inner scaffold coupled to the outer scaffold via one or more tethers, comprising a body extending between a proximal end and a distal end, and defining a central opening therethrough, the inner scaffold positioned within the outer scaffold and the body configured for expansion within the outer scaffold and further configured to receive and engage a distal portion of the left atrial appendage within the central opening after inversion of the distal portion of the left atrial appendage;
- wherein the body of the inner scaffold does not apply direct radial pressure to the outer scaffold when both the outer scaffold and the inner scaffold are expanded, and the outer scaffold further comprises an occluder membrane coupled thereto, the occluder membrane configured to occlude an orifice of the left atrial appendage upon expansion of the occluder membrane and inhibit bidirectional flow therethrough.

12. The system of claim 11, further comprising:
- a vacuum tube defining a vacuum tube lumen therethrough, the vacuum tube having a suction flange at its distal end and configured for insertion into a lumen of the catheter.

13. The system of claim 12, wherein when a vacuum is applied through the vacuum tube and the suction flange is attached to the distal portion of the left atrial appendage, the vacuum tube can be withdrawn in a direction away from the distal portion to invert the distal portion.

14. The system of claim 12, further comprising:
- a vacuum source coupled to the vacuum tube, the vacuum source operable to generate a vacuum within the vacuum tube lumen to facilitate engagement of the distal portion of the left atrial appendage using the suction flange of the vacuum tube; and
- an inflation source coupled to the catheter, the inflation source operable to inflate and/or deflate the balloon.

15. The system of claim 11, wherein the outer scaffold is configured for self-expansion within the interior of the left atrial appendage and further configured to conform to the interior of the left atrial appendage.

16. The system of claim 11, further comprising:
- a sheath configured for placement around at least part of the catheter and further configured to receive the double stent assembly in a compressed configuration therein.

17. The system of claim 11, further comprising:
- one or more memory arms coupled to the outer scaffold or the occluder membrane, the one or more memory arms configured to receive and retain at least a portion of the left atrial appendage; and
- a flap membrane coupled to the outer scaffold or the occluder membrane, the flap membrane configured to cover the one or more memory arms.

18. A double stent assembly for occluding a left atrial appendage, the double stent assembly comprising:
- an outer scaffold configured for expansion and to be anchored within an interior of a left atrial appendage;
- an inner scaffold comprising a body extending between a proximal end and a distal end, and defining a central opening therethrough, the inner scaffold positioned within the outer scaffold and the body configured for expansion within the outer scaffold and further configured to receive and engage a distal portion of the left atrial appendage within the central opening after inversion of the distal portion of the left atrial appendage;
- one or more tethers coupled to the outer scaffold and the inner scaffold, the one or more tethers configured to retain the inner scaffold within the outer scaffold; and
- an occluder membrane coupled to the outer scaffold, the occluder membrane configured to occlude an orifice of the left atrial appendage upon expansion of the occluder membrane and inhibit bidirectional flow therethrough;
- wherein the body of the inner scaffold does not apply direct radial pressure to the outer scaffold when both the outer scaffold and the inner scaffold are expanded;
- wherein the double stent assembly is configured for placement upon a balloon coupled to a catheter such that inflation of the balloon expands the body of the inner scaffold; and
- wherein the outer scaffold is configured for self-expansion within the interior of the left atrial appendage and further configured to conform to the interior of the left atrial appendage.

19. The double stent assembly of claim 18, wherein the occluder membrane is configured to prevent emboli from within the interior of the left atrial appendage from being released from the interior of the left atrial appendage.

20. The double stent assembly of claim 18, wherein the occluder membrane comprises a valve configured to receive a catheter therethrough.

\* \* \* \* \*